US012078773B2

(12) United States Patent
Ohayon

(10) Patent No.: US 12,078,773 B2
(45) Date of Patent: Sep. 3, 2024

(54) METHOD FOR PREVENTING INFECTIOUS DISEASE OUTBREAKS IN NURSING HOMES AND HOSPITALS DUE TO GLOBAL WARMING AND RESISTANCES TO MEDICATION

(71) Applicant: Jacques Jacob Ohayon, Wayne, NJ (US)

(72) Inventor: Jacques Jacob Ohayon, Wayne, NJ (US)

( * ) Notice: Subject to any disclaimer, the term of this patent is extended or adjusted under 35 U.S.C. 154(b) by 689 days.

(21) Appl. No.: 17/082,511

(22) Filed: Oct. 28, 2020

(65) Prior Publication Data

US 2021/0149078 A1     May 20, 2021

Related U.S. Application Data

(60) Provisional application No. 62/974,204, filed on Nov. 18, 2019.

(51) Int. Cl.
| | | |
|---|---|---|
| *G01W 1/02* | (2006.01) | |
| *A61B 5/00* | (2006.01) | |
| *F24F 11/30* | (2018.01) | |
| *F24F 11/50* | (2018.01) | |
| *F24F 130/10* | (2018.01) | |

(52) U.S. Cl.
CPC .............. *G01W 1/02* (2013.01); *A61B 5/7465* (2013.01); *F24F 11/30* (2018.01); *F24F 11/50* (2018.01); *F24F 2130/10* (2018.01); *G01W 2201/00* (2013.01)

(58) Field of Classification Search
CPC ..... G01W 1/02; G01W 2201/00; F24F 11/50; F24F 11/30; F24F 2130/10; A61B 5/7465

USPC .......................................................... 340/601
See application file for complete search history.

(56) References Cited

U.S. PATENT DOCUMENTS

| | | | | |
|---|---|---|---|---|
| 4,856,227 A | * | 8/1989 | Oglevee ................. | A01G 9/247 165/223 |
| 4,858,377 A | * | 8/1989 | Oglevee ................. | A01G 9/247 165/223 |
| 2014/0326801 A1 | * | 11/2014 | Upadhyaya .......... | G01N 33/246 239/69 |

(Continued)

*Primary Examiner* — Naomi J Small

(57) ABSTRACT

This invention addresses the problem of Global Warming, expressed as the environmental condition of unintended and imperceptible levels of Vapor Pressure Deficit, (VPD) in Nursing Homes and Hospitals and Psychiatric Facilities. The invention teaches an art form which addresses Global Warming as expressed by Vapor Pressure deficit and resistance to medication. The invention identifies the ideal conditions for fungal and bacteria growth and in particular a new highly resistant fatal form of *Candida* Fungus, referred to as *Candida auris* (*C. auris*). Existing HVAC technology does not address this problem, since it is novel in that it identifies a unique interaction between Global Warming with the problem of resistances to medication and the neurological causes of Suicide. The invention is also novel and unobvious in that it teaches an art form indicating that certain levels of imperceptible VPD require continued HVAC, A/C dehumidification and temperature reduction even throughout tepid temperatures when such equipment may be turned off. As well as teaches an art form to alert medical staff and administration as to when these conditions are occurring and help plan treatments during periods of favorable ambient indoor and outdoor environmental conditions.

11 Claims, 8 Drawing Sheets

(56) References Cited

U.S. PATENT DOCUMENTS

2020/0281128 A1\* 9/2020 Erickson .................. A01G 9/18
2021/0059276 A1\* 3/2021 Valverde ................. A23L 11/33

\* cited by examiner

VAPOR PRESSURE DEFICIT CHART

VPD AND RELATIVE HUMIDITY

OCTOBER 2019 TEMPERATURE HUMIDITY AND VAPOR PRESSURE DEFICIT

| | TEMP | HUMIDITY | VPD | |
|---|---|---|---|---|
| 1 | 81 | 60 | 1.46 | ** |
| 2 | 91 | 64 | 1.82 | |
| 3 | 62 | 51 | 0.94 | |
| 4 | 62 | 46 | 1.04 | |
| 5 | 59 | 38 | 1.07 | |
| 6 | 69 | 46 | 1.33 | ** |
| 7 | 74 | 59 | 1.19 | |
| 8 | 63 | 53 | 0.93 | |
| 9 | 57 | 51 | 0.79 | |
| 10 | 69 | 51 | 1.2 | ** |
| 11 | 65 | 52 | 1.04 | |
| 12 | 69 | 52 | 1.18 | |
| 13 | 66 | 46 | 1.19 | |
| 14 | 72 | 52 | 1.3 | |
| 15 | 64 | 41 | 1.22 | ** |
| 16 | 65 | 41 | 1.26 | ** |
| 17 | 56 | 49 | 0.79 | |
| 18 | 55 | 45 | 0.82 | |
| 19 | 63 | 35 | 1.29 | ** |
| 20 | 55 | 37 | 0.94 | |
| 21 | 66 | 47 | 1.17 | |
| 22 | 59 | 46 | 0.93 | |
| 23 | 65 | 44 | 1.19 | |
| 24 | 69 | 37 | 1.55 | ** |
| 25 | 65 | 40 | 1.28 | ** |
| 26 | 64 | 45 | 1.13 | |
| 27 | 63 | 51 | 0.97 | |
| 28 | 62 | 53 | 0.9 | |
| 29 | 59 | 53 | 0.81 | |
| 30 | 64 | 56 | 0.91 | |
| 31 | 73 | 60 | 1.12 | |

| VPD | OCTOBER | SEPTEMEBR 2019 |
|---|---|---|
| AVERAGE | 1.121 | 1.441 |
| SD | 0.23068 | 0.26223 |

Statistical Test for Difference in Two Means VPD Only
two tailed t-test p less than .0001
t=5.06    95% C.I.=.1938-.4467
df=59

| | OCTOBER READINGS | |
|---|---|---|
| | AVERAGE | SD |
| TEMP | 65.35 | 7.368 |
| HUMIDITY | 48.41 | 7.201 |

DEVICES USED IN THE EMBODIMENT OF ENCLOSED INVENTION

FIG. 8
Vapor Pressure Deficit in a Nursing Home

| DATE | TIME | TEMP C | HUMIDITY | VPD |
|---|---|---|---|---|
| 9/4/2020 | 18:44 | 23.4 | 55 | 1.29 |
| 9/4/2020 | 18:45 | 23.4 | 55 | 1.29 |
| 9/4/2020 | 18:46 | 23.5 | 54.6 | 1.31 |
| 9/4/2020 | 18:48 | 23.5 | 54.4 | 1.31 |
| 9/4/2020 | 18:49 | 23.4 | 54.7 | 1.3 |
| 9/4/2020 | 18:50 | 23.4 | 54.6 | 1.3 |
| 9/4/2020 | 18:51 | 23.2 | 55.3 | 1.26 |
| 9/4/2020 | 18:52 | 23.2 | 55.3 | 1.26 |
| 9/4/2020 | 18:53 | 23.2 | 55.4 | 1.26 |
| 9/4/2020 | 18:54 | 23.2 | 55.7 | 1.25 |
| 9/4/2020 | 18:55 | 23.1 | 55.8 | 1.24 |
| 9/4/2020 | 18:56 | 23.1 | 55.9 | 1.24 |
| 9/4/2020 | 18:58 | 23.1 | 56.2 | 1.23 |
| 9/4/2020 | 18:59 | 23.1 | 56.3 | 1.23 |
| 9/4/2020 | 19:00 | 23.1 | 56 | 1.24 |
| 9/4/2020 | 19:01 | 23.1 | 55.7 | 1.24 |

METHOD FOR PREVENTING INFECTIOUS DISEASE OUTBREAKS IN NURSING HOMES AND HOSPITALS DUE TO GLOBAL WARMING AND RESISTANCES TO MEDICATION

BACKGROUND

Nearly 35,000 people in the United States die each year from drug-resistant infections. One problem Worldwide and in particular in New York and New Jersey is the new and virulent strain, *Candida auris* (*C. auris*), which is a member of the *Candida* genus of funguses. The infection caused by this strain is referred to as *Candidiasis auris*, which is highly resistant to medication and often fatal. Outbreaks of *C. auris* are mostly found in hospitals and nursing homes. In 2019, over 64 hospitals and 103 nursing homes reported deaths due to *C. auris*.

According to the Centers of Disease Control (CDC) every 11 seconds someone the United States gets a resistant infection, and someone dies every 15 minutes. *C. auris* is one of the newer and more difficult to understand fungal infections. The strain was first discovered in 2009 in Japan.

The first clinical report of *C. auris* infection from the CDC, occurred in June 2016, with 13 cases reported. It was found that 71% of the cases were drug resistant. Four years later the case count in the US has grown to over 1,200 for the first three quarters of 2020.

It is estimated that approximately half the patients who contract *C. auris* die within 90 days. The CDC has also demonstrated that *C. auris* level of resistance is higher than most funguses. It is also extremely hard to treat once it invades the body. Most class one and class two anti-fungal medications are not effective. It is also highly contagious and spreads very quickly among the vulnerable population in healthcare facilities.

It is possible that the administration of powerful anti-fungal agents may contribute to an outbreak by killing off weaker strains and leaving stronger strains to proliferate. In some cases, in patients who are already vulnerable due to pre-existing illness, the infection invades the blood stream and patients become septic. The worldwide death rate among patients with *C. auris* is 60%.

*C. auris* has dangerous features similar to those found in bacteria which sticks and grows on surfaces thus causing nosocomial infections in healthcare facilities. It can also be spread by healthcare workers to patients and also among patients. According to Consumer Reports Jul. 29, 2019, the outbreaks are mysterious as they often occur in Healthcare facilities with extremely strict infection control and within exceptionally clean environments.

The New York Times, Nov. 13, 2019, reported that *C. auris* outbreaks have occurred suddenly with entire wards of patients becoming ill and dying quickly, even after being given the most advanced forms of medical treatment and anti-fungal agents. Often patients have lesions that can be seen through-out their bodies due to a *C. auris* infection. The infection has been reported in 120 countries included the United States. The Center of Disease Control report, Tracking *Candida Auris*, July 2020, indicates that for 2020, the total case count for hospitalized patients is 1,272 for the United States. An additional 2,493 cases were found to be colonized for *C. auris*.

*C. auris* is the newest and most drug resistant strain seen in hospitals from the *Candida* class of fungal infections. Only three classes of drugs are available to treat C. *Auris*: azoles, echinocandins and amphotericin B.

The question now becomes why has *C. auris* suddenly emerged and why is it so virulent and drug resistant. Like the fungal growth seen in typical moist or humid environments our research has surprisingly answered this question by showing that nursing homes can actually resemble the conditions in environmental Greenhouses due to the phenomena of Global Warming, (see FIG. 8).

The data in FIG. 8 is a snapshot of a nursing home ambient temperature, Celsius 23 degrees, and relative humidity between 54-56 percent on Sep. 4, 2020. During these periods, which converts to 73 degrees Fahrenheit, it is possible that the HVAC A/C units may be off, thereby causing a vulnerability in the facility due to the imperceptible nature of VPD.

Lockhart, et al, 2017 Journal of Clinical Infectious Diseases Vol 64 Issue 2, using whole genome sequencing, together with epidemiological analysis showed that *C. auris* is also unique since it was found simultaneously on three continents between 2012-2015, India, South-Africa, and Venezuela, and offers support for the view that was caused by environmental changes. An analysis from Johns Hopkins University, Oct. 21, 2020, argues that Global Warming may be responsible for its emergence on the planet.

As an indicator of a serious adverse effect of Global Warming, we seek to detect and measure, Vapor Pressure Deficient (VPD) in nursing homes and hospitals (see FIG. 1). VPD is measured in kilopascals (Kpa) where one kilopascal is equal to one thousand Newtons per square meters. A VPD between 1.2 and 1.5 Kpa is considered the ideal confluence of humidity and temperature resulting in flowering in Greenhouse plants and vegetation (see FIG. 2).

A Greenhouse will typically adjust temperature levels and humidity simultaneously, for optimal vegetation or flowering. Our invention initiates an alert in the range of 1.2-1.5 of VPD. We selected this range since *C. auris* is an incredibly resistant fungus that alludes explanation, together with the fact that an unintended and imperceptible VPD in this range is possibly an environmental anomaly which expresses conditions due to Global Warming. The range 1.2 to 1.5, as mentioned above, is also biologically, the ideal VPD for flowering in a Greenhouse environment. This translates to an ideal environment for *C. auris* growth when detected indoors due to a "perfect storm" of temperature and humidity gradients. This reduces moisture absorption of the air and at the same time, especially during the fall months, finds HVAC, Air Conditioner (A/C) units turned off.

FIG. 3 illustrates the transient nature of VPD when a consistent level of humidity (50%) is present. We see that as the temperature drops from 90 to 70 degrees Fahrenheit (F), conditions ideal for flowering occurs at the lower temperature. In this Figure we see that a VPD of 1.3 Kpa emerges at 70 degrees F. This would not likely be detected by a nursing home facility and A/C units could also be shut down at 70 degrees F., and 50% humidity, which would also contribute to the incidence of dangerous VPD.

Global Warming is related to this phenomena since ambient moisture levels due to the melting Polar Regions of the world, increase humidity levels. As such, humidity at only 40% to 50% during fall months, where tepid temperatures can now range between 60 to 70 degrees F., in the Eastern United States, and throughout the year in other parts of the country, greatly increases the potential for indoor environments to enter VPD in the 1.2-1.5 range (see FIG. 4). FIG. 4 shows a statistically significant difference in outdoor VPD from September to October. This supports our view that VPD is variable and fluctuates during the fall months with transient temperature changes and humidity.

Important research by Barkhordarian, et al, Nature Scientific Reports 2019, 9:15331, offers an important insight into the reality of Global Warming and its specific impact on increasing VPD. This research report can be seen as supporting this art form. Whereby VPD is desirable in Greenhouses for the growth of vegetation and flowering, this condition could cause a potentially dangerous environment in Nursing Homes and Hospitals where the rapid propagation of *C. auris*, may result.

The practice of this art form also creates a safe to medicate, or not safe to medicate paradigm, based on whether a patients environment is in VPD range of 1.2 to 1.5, indicating an adverse environmental event. Outbreaks and resistances are believed to be more likely under these conditions since it could contribute to the propagation of the stronger strains when treating with an anti-fungal medication.

Suicide in the United States was responsible for 48, 195 deaths in 2021 which is one death every 11 minutes.

Recent research has indicated that changes in Vapor Pressure Deficit and Humidity may be related to Suicide.

SUMMARY OF THE DISCLOSED TECHNOLOGY

The purpose of this invention is to provide alerts to medical personnel to notify them of the occurrence of dangerous and undetectable interaction between humidity levels and temperature, i.e., Vapor Pressure Deficient. Alerts will notify medical personnel with regards to dangerous environmental conditions in Nursing Homes and Hospitals. The alerts are particularly important during tepid weather conditions when A/C units are turned off. The alerts will take the form of text messages, emails, and phone calls. Facility personnel including medical, and administration will also have the ability to login to view readings. (FIG. 5).

The invention also teaches an art form, where physicians consider the indoor ambient humidity and temperature, and the interaction of such conditions, prior to treatment with medication associated with resistances.

Description of the Problems that this Invention Solves

This invention addresses the problem of undetected levels of humidity (VPD) combining with the phenomena of resistances to medication, which creates the ideal conditions for funguses and other microbes to proliferate. Existing technology does not address these problems since this is a novel and unobvious approach, unknown to the medical science and introduces a unique interaction between Global Warming with the problem of resistance to medication. By analyzing this unique interaction with Global Warming, this approach brings the concept of VPD into Nursing Homes and the Hospital environment, as a new art form.

It is also novel in that it teaches an art form to alert medical personnel as to insidious and potentially dangerous conditions which may be occurring. This can help plan treatments on days of more favorable ambient in-door and possibly outdoor weather conditions, avoiding periods where the facility is experiencing dangerous levels of VPD.

Description of How the Invention is an Improvement Over Existing Technology

Currently existing technology does not comprehend the interaction between Global Warming expressed through VPD and Resistances to Medication, leading to fatal outbreaks of *C. auris* and other microbes. Our technology introduces a process to determine when a facilities A/C must be turned on or off, saving the facility on the cost of cooling. As we have shown VPD is largely undetectable using existing methods, because if this, knowing when to treat or not to treat, is difficult to determine. Our research indicates that the large number of deaths in nursing homes and hospitals, due to *C. auris* during the more tepid temperatures of the fall, together with the presence of VPD, could potentially be reduced by measuring and reporting VPD.

Description of the Benefits of this Invention to its Users

The benefits of this invention are that it could reduce the occurrence of outbreaks of fatal fungal *Candidiasis auris* and potentially other microbes. It could also help doctors select the best ambient conditions for which to treat resistant conditions and avoid harming patients and causing outbreaks. The invention will help the medical staff and administration decide when it is safe to turn down the expensive A/C units during cooler temperatures, and when A/C must be kept on for patient safety in Nursing Homes and Hospitals.

DESCRIPTION OF THE INVENTION

The following formula expresses VPD:

$$VPD=SVP \times (1-RH/100)$$

Where $SVP=610.78 \times e\hat{}(T/(T+238.3) \times 17.2694))$ T is in degrees Celsius. The result, SVP, is in pascals (divide by 1000 to get kPa); e is a mathematical constant called Euler's Number, approximately equal to 2.71828. Where RH is relative humidity and SVP is saturated vapor pressure.

SVP is critical to this art form. It is an important factor for determining VPD and can be illustrated in FIG. 6. We can see that SVP is dependent on ambient temperature. SVP increases as the temperature rises, since warmer air (lower pressure) can absorb a greater amount of moisture.

VPD is the saturated Vapor Pressure minus the actual Vapor Pressure (SVP-VP (actual), and VP actual=(RH*SVP/100. We may apply the formula VPD=(1−RH/100))*SVP). Alternatively: VPD=(1−(RH/100))*SVP).

FIG. 7 shows a high-level block diagram of devices used in embodiments of the disclosed technology. Device 600 comprises a processor 650 that controls the overall operation of the computer by executing the device's program instructions which define such operation. The device's program instructions may be stored in a storage device 620 (e.g., magnetic disk, database) and loaded into memory 630 when execution of the console's program instructions is desired. Thus, the device's operation will be defined by the device's program instructions stored in memory 630 and/or storage 620, and the console will be controlled by processor 650 executing the console's program instructions. A device 600 also includes one, or a plurality of, input network interfaces for communicating with other devices via a network (e.g., the internet).

The device 600 further includes an electrical input interface. A device 600 also includes one or more output network interfaces 610 for communicating with other devices. Device 600 also includes input/output 640 representing devices, which allow for user interaction with a computer (e.g., display, keyboard, mouse, speakers, buttons, etc.). One skilled in the art will recognize that an implementation of an actual device will contain other components as well, and that FIG. 7 is a high-level representation of some of the components of such a device, for illustrative purposes. It should also be understood by one skilled in the art that the method, data, and devices depicted in FIGS. 1 and 6 may be implemented on a device such as is shown in FIG. 7.

Further, it should be understood that all subject matter disclosed herein is directed at, and should be read only on, statutory, non-abstract subject matter. All terminology should be read to include only the portions of the definitions which may be claimed. By way of example, "computer readable storage medium" is understood to be defined as only non-transitory storage media.

BRIEF DESCRIPTION OF DRAWINGS

FIG. 8 Is a print-out of the date, time, temperature, humidity and VPD in an actual Nursing Home.

Figure 1:
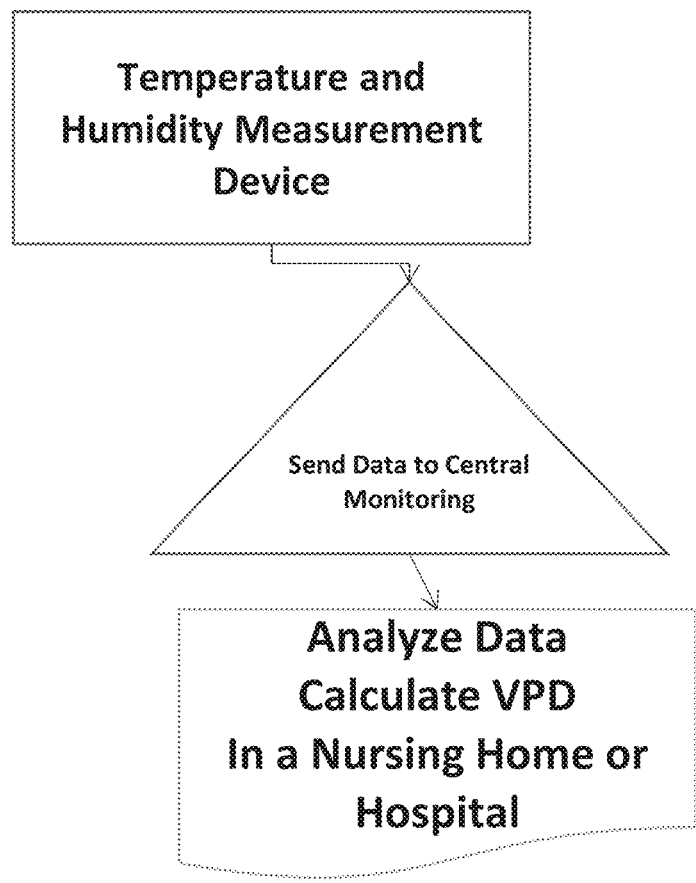
FIG. 1 is a flow chart of a method of carrying out embodiments of the disclosed technology.
Figure 2:
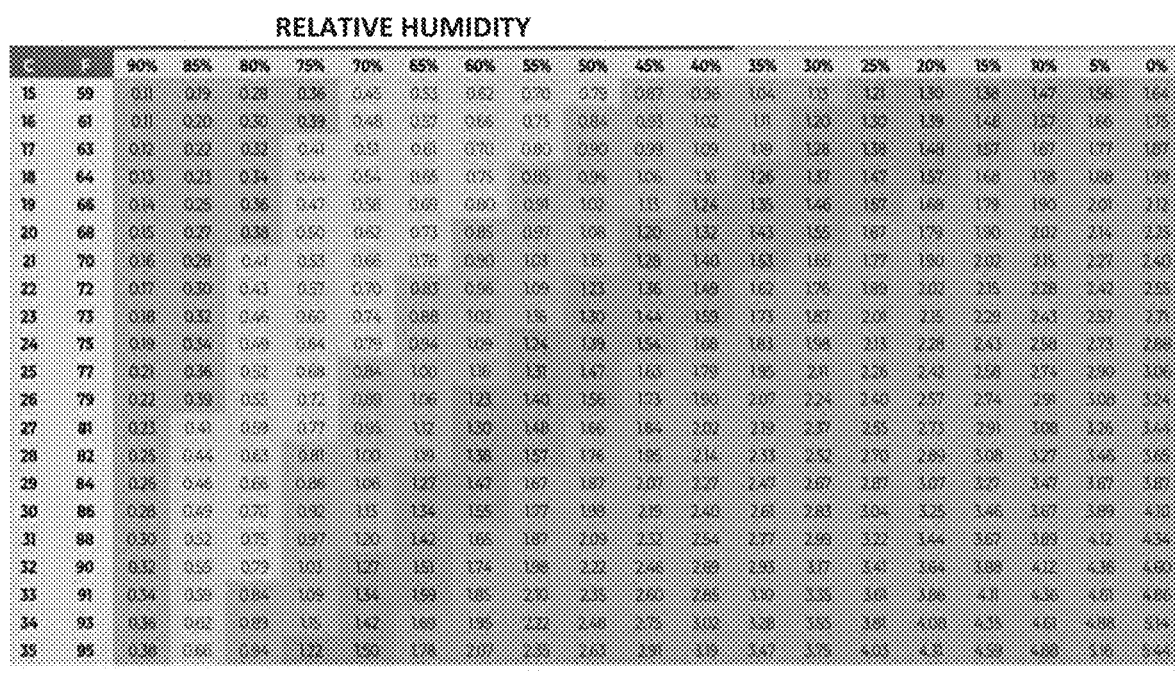
FIG. 2 Is a chart of the gradient of Fahrenheit temperature and Relative Humidity, illustrated with VPD. Dangerous levels of VPD are indicated as between 1.2-1.5 and highlighted when detected in Nursing Homes and Hospitals.
Figure 3:
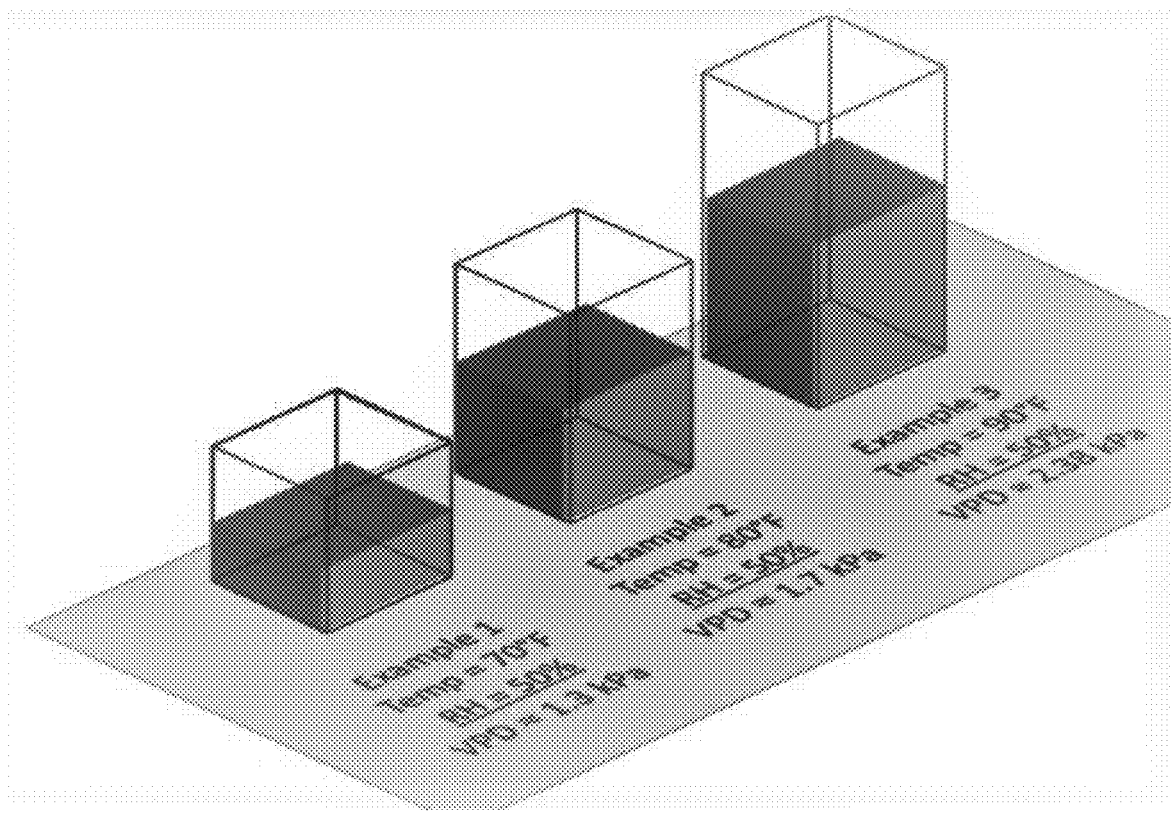
FIG. 3 Is an example of how VPD changes across different levels temperature and a consistent relative humidity, in order to better explain the importance of the invention.
Figure 4:
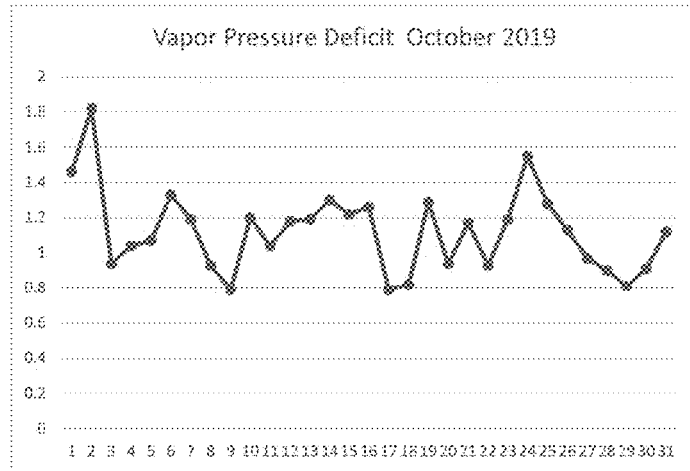
FIG. 4 Is a comparison of VPD for October and September of 2019 in Northern New Jersey.
Figure 5:
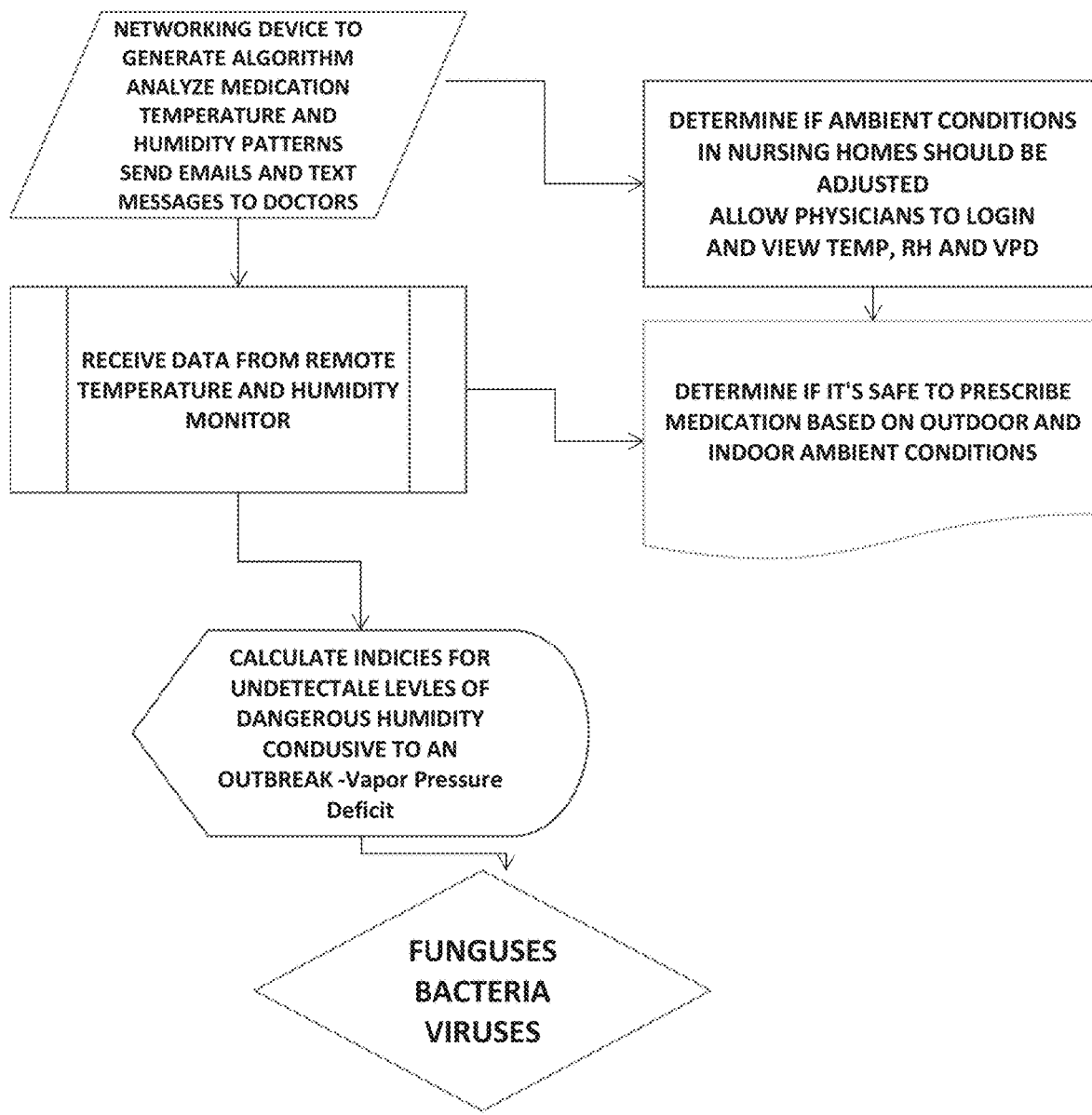
FIG. 5 Is a detailed description of the inventive steps taken and art form to create the invention, including evaluating ambient conditions, alerting with texting, emailing, and calling interested parties in Nursing Homes and Hospitals.
Figure 6:
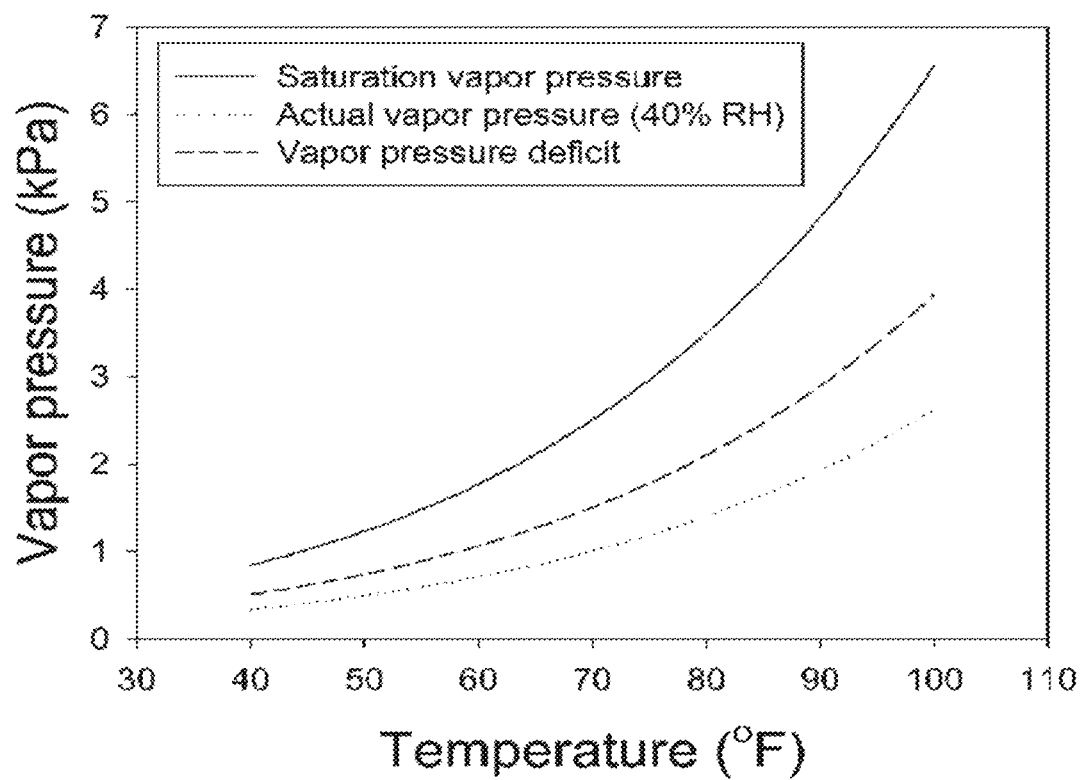
FIG. 6 Is an illustration of the relationship between SVP and VPD and the point where A/C units may be turned off causing VPD at a level of 1.2-1.5.
Figure 7:
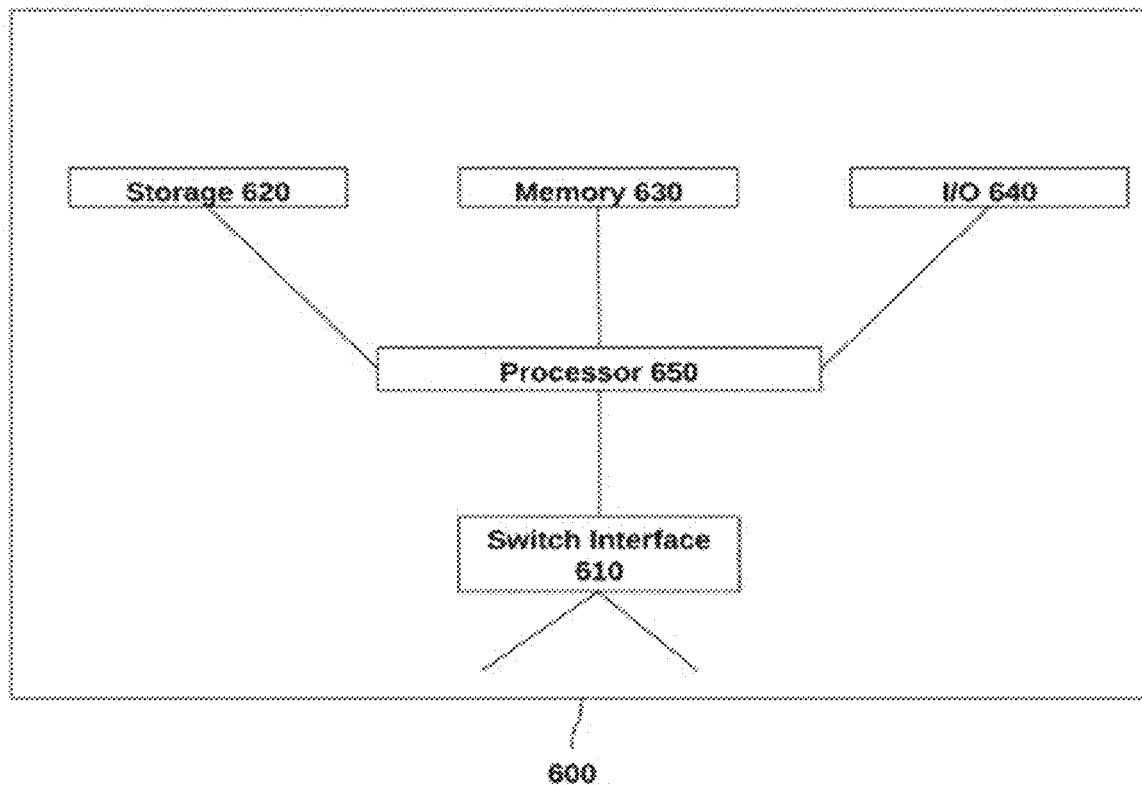
FIG. 7 Is a high-level block diagram of devices used in embodiments of the disclosed technology.

I claim:

1. A computer implemented method of measuring the effects of Global Warming in Nursing Homes Hospitals, and inpatient and outpatient psychiatric clinics, comprising the steps of:
   measuring or receiving a digital reading of temperature and relative humidity and determining Vapor Pressure Deficit (VPD);
   determining a level of temperature and relative humidity in order to establish VPD fluctuation across a 24-hour period for at least one day;
   creating a report across a gradient of temperature and relative humidity in order to arrive at VPD in an indoor facility following as close as possible to the actual temperature and relative humidity;
   outputting through an input/output device, if indicated, an alert reflecting that the facility has entered a dangerous level of VPD; and
   wherein an input is received indicating whether the VPD levels are normal, and wherein a digital determination of an alert must be sent indicating that the VPD is abnormal; and during a step of comparing, said level is used to determine if said VPD levels represent an abnormal and dangerous level of VPD in nursing homes and hospitals or other medical facilities.

2. The computer implemented method as claimed in claim 1, wherein when VPD is within a pre-defined threshold indicating a dangerous environmental event is occurring indoors or outdoors resulting in notification via email, text or telephonically, through a network interface, to alert medical facility managers or physicians as to a potentially dangerous environmental situation.

3. The computer implemented method as claimed in claim 1, further permitting appropriate notification of a dangerous VPD found in the facility to known levels which are conducive to flowering and the propagation of microbes such as *Candida Auris*.

4. The computer implemented method of claim 3, wherein an alert is prepared when it is determined that a facility has arrived at predetermined levels of VPD and Medical Staff and Administrators must be contacted by email, text or telephonically.

5. The computer implemented method of claim 4, wherein the facility must be directed, through a processor, to maintain HVAC system for air conditioning for cooling and dehumidification or heating to eliminate levels of VPD.

6. The computer implemented method of claim 1, wherein a determination is made by comparing levels of VPD to a plurality of different levels for determining whether such levels differ from levels of VPD that are representative of a healthy environment in a Nursing Home or Hospital or when treating medical or psychiatric patients.

7. The computer implemented method of claim 6, wherein said determined levels of VPD are related to specific forms of Global Warming due to excessive greenhouse gases in the environment and such excessive greenhouse gases cause high humidity in a context of lower temperatures, lower VPD levels and higher pressure impacting neurological functioning in medical patients being treated with Psychiatric medication.

8. The computer implemented method of claim 3, wherein a determined fungal outbreak of *C. auris* is related to fluctuations of measured relative humidity and temperature and a confluence of such, to arrive at a specific change in VPD and based on the occurrence of serious illness in patients in Nursing Homes, Hospitals Clinics or Doctor's Offices.

9. The computer implemented method of claim 6, wherein said input received determines whether the facility is being impacted by Global Warming as reflected by VPD and that ambient conditions in the facility must be altered to prevent an outbreak of serious disease such as *C. auris* and potentially other medical and psychiatric conditions.

10. The computer implemented method of claim 2, wherein an adverse undetectable environmental event occurs as reflected by VPD, requires the notification via text message, email, or telephone call, and is further suggested by an occurrence of any current fungal outbreaks based on receiving information of the presence of such disease in the facility such as a Nursing Home or Hospital.

11. The computer implemented method of claim 1, wherein medical staff and administrators can log into an establish server to view said VPD readings to assess the safety of treating *C. auris* and other infectious agents and chronic illnesses to determine a safe ambient environment and whether a facility is being impacted by Global Warming.

* * * * *